US008936921B2

(12) United States Patent
Hicke et al.

(10) Patent No.: US 8,936,921 B2
(45) Date of Patent: Jan. 20, 2015

(54) METHODS OF ISOTHERMAL AMPLIFICATION USING BLOCKED PRIMERS

(71) Applicant: Great Basin Scientific, West Valley, UT (US)

(72) Inventors: Brian Hicke, Snyderville, UT (US); Robert D. Jenison, Boulder, CO (US); Madeline West, Boulder, CO (US)

(73) Assignee: Great Basin Scientific Corporation, West Valley, UT (US)

( * ) Notice: Subject to any disclaimer, the term of this patent is extended or adjusted under 35 U.S.C. 154(b) by 0 days.

(21) Appl. No.: 13/908,827

(22) Filed: Jun. 3, 2013

(65) Prior Publication Data
US 2014/0017730 A1     Jan. 16, 2014

Related U.S. Application Data

(63) Continuation of application No. PCT/US2013/026202, filed on Feb. 14, 2013.

(60) Provisional application No. 61/598,648, filed on Feb. 14, 2012.

(51) Int. Cl.
*C12Q 1/68* (2006.01)
*C12P 19/34* (2006.01)

(52) U.S. Cl.
CPC ............... *C12Q 1/686* (2013.01); *C12P 19/34* (2013.01); *C12Q 1/68* (2013.01)
USPC ...................................... 435/91.2; 435/287.2

(58) Field of Classification Search
CPC .... C12Q 1/6844; C12Q 1/686; C12Q 1/6848; C12Q 1/6806; C12Q 1/6846; C12Q 1/682; C12P 19/34; C12P 19/00; C12P 17/06; C12P 17/10; C12P 21/00; C12P 21/02
USPC .............................................. 435/91.2, 287.2
See application file for complete search history.

(56) References Cited

U.S. PATENT DOCUMENTS

| 4,876,187 A | 10/1989 | Duck et al. |
| 5,011,769 A | 4/1991 | Duck et al. |
| 5,403,711 A | 4/1995 | Walder et al. |
| 6,251,600 B1 | 6/2001 | Winger et al. |
| 7,135,291 B2 | 11/2006 | Sagawa et al. |
| 7,824,890 B2 * | 11/2010 | Hoser et al. ................... 435/91.2 |
| 2006/0154286 A1 | 7/2006 | Kong et al. |
| 2006/0199178 A1 | 9/2006 | Kobayashi et al. |
| 2010/0167353 A1 | 7/2010 | Walder et al. |

FOREIGN PATENT DOCUMENTS

WO    WO 2009/135093 A2    11/2009

OTHER PUBLICATIONS

Dobosy et al. (BMC Biotechnology, 2011, 11:80, p. 1-18).*
iQ SYBR™ Green Supermix, (BioRad, 2014, p. 1).*
Nowotny et al. (EMBO Journal, 2008, 27, p. 1172-1181).*
International Search Report, International Application No. PCT/US2013/026202, dated Apr. 25, 2013 (4 pages).
Dobosy et al. BMC Biotechnology 2011, RNase H-dependent PCR (rhPCR): improved specificity and single nucleotide polymorphism detection using blocked cleavable primers.

* cited by examiner

*Primary Examiner* — Stephanie K Mummert
(74) *Attorney, Agent, or Firm* — Brinks Gilson & Lione; Ryan L. Marshall

(57) ABSTRACT

Methods for rapidly detecting clinically relevant mutations in the infectious genome of an agent are disclosed. The methods include use of a novel target and temperature dependent RNase H mediated cleavage of blocked DNA primers to initiate isothermal helicase-dependent amplification of a target sequence such as a sequence in the rpoB gene.

22 Claims, 3 Drawing Sheets

US 8,936,921 B2

SEQUENCE LISTING

```
<160> NUMBER OF SEQ ID NOS: 27

<210> SEQ ID NO 1
<211> LENGTH: 26
<212> TYPE: DNA
<213> ORGANISM: Artificial Sequence
<220> FEATURE:
<223> OTHER INFORMATION: Primers

<400> SEQUENCE: 1
cgatcaagga gttcttcggc raccag                                          26

<210> SEQ ID NO 2
<211> LENGTH: 25
<212> TYPE: DNA
<213> ORGANISM: Artificial Sequence
<220> FEATURE:
<223> OTHER INFORMATION: Primers

<400> SEQUENCE: 2
ggcacgctca cgtgacagar ccgcc                                           25

<210> SEQ ID NO 3
<211> LENGTH: 20
<212> TYPE: DNA
<213> ORGANISM: Artificial Sequence
<220> FEATURE:
<223> OTHER INFORMATION: Primers

<400> SEQUENCE: 3
cgatcaagga gttcttcggc                                                 20

<210> SEQ ID NO 4
<211> LENGTH: 19
<212> TYPE: DNA
<213> ORGANISM: Artificial Sequence
<220> FEATURE:
<223> OTHER INFORMATION: Primers

<400> SEQUENCE: 4
ggcacgctca cgtgacaga                                                  19

<210> SEQ ID NO 5
```

```
<211> LENGTH: 20
<212> TYPE: DNA
<213> ORGANISM: Artificial Sequence
<220> FEATURE:
<223> OTHER INFORMATION: Primers

<400> SEQUENCE: 5
ctgatccaaa accagatccg                                                      20

<210> SEQ ID NO 6
<211> LENGTH: 20
<212> TYPE: DNA
<213> ORGANISM: Artificial Sequence
<220> FEATURE:
<223> OTHER INFORMATION: Primers

<400> SEQUENCE: 6
tacacgatct cgtcgctaac                                                      20

<210> SEQ ID NO 7
<211> LENGTH: 21
<212> TYPE: DNA
<213> ORGANISM: Artificial Sequence
<220> FEATURE:
<223> OTHER INFORMATION: Primers

<400> SEQUENCE: 7
atgtcgcgga tggagcgggt g                                                    21

<210> SEQ ID NO 8
<211> LENGTH: 21
<212> TYPE: DNA
<213> ORGANISM: Artificial Sequence
<220> FEATURE:
<223> OTHER INFORMATION: Primers

<400> SEQUENCE: 8
gagccgatca gaccgatgtt g                                                    21

<210> SEQ ID NO 9
<211> LENGTH: 32
<212> TYPE: DNA
<213> ORGANISM: Artificial Sequence
<220> FEATURE:
<223> OTHER INFORMATION: Primers

<400> SEQUENCE: 9
tacagatgaa tatattgcag caactgrgtt ca                                        32

<210> SEQ ID NO 10
<211> LENGTH: 36
<212> TYPE: DNA
<213> ORGANISM: Artificial Sequence
<220> FEATURE:
<223> OTHER INFORMATION: Primers

<400> SEQUENCE: 10
ttgagctgta tcaggatcaa aataatactc rctcac                                    36

<210> SEQ ID NO 11
<211> LENGTH: 26
<212> TYPE: DNA
<213> ORGANISM: Artificial Sequence
<220> FEATURE:
<223> OTHER INFORMATION: Primers

<400> SEQUENCE: 11
```

```
tacagatgaa tatattgcag caactg                                          26

<210> SEQ ID NO 12
<211> LENGTH: 30
<212> TYPE: DNA
<213> ORGANISM: Artificial Sequence
<220> FEATURE:
<223> OTHER INFORMATION: Primers

<400> SEQUENCE: 12
ttgagctgta tcaggatcaa ataatactc                                       30

<210> SEQ ID NO 13
<211> LENGTH: 36
<212> TYPE: DNA
<213> ORGANISM: Artificial Sequence
<220> FEATURE:
<223> OTHER INFORMATION: Primers

<400> SEQUENCE: 13
acagatgaat atattgcagc aactggttca gttatt                               36

<210> SEQ ID NO 14
<211> LENGTH: 31
<212> TYPE: DNA
<213> ORGANISM: Artificial Sequence
<220> FEATURE:
<223> OTHER INFORMATION: Primers

<400> SEQUENCE: 14
tacagatgaa tatattgcag caactggttc a                                    31

<210> SEQ ID NO 15
<211> LENGTH: 35
<212> TYPE: DNA
<213> ORGANISM: Artificial Sequence
<220> FEATURE:
<223> OTHER INFORMATION: Primers

<400> SEQUENCE: 15
ttgagctgta tcaggatcaa ataatactc ctcac                                 35

<210> SEQ ID NO 16
<211> LENGTH: 26
<212> TYPE: DNA
<213> ORGANISM: Artificial Sequence
<220> FEATURE:
<223> OTHER INFORMATION: Primers

<400> SEQUENCE: 16
ggatagacgt catatgaagg tgtgct                                          26

<210> SEQ ID NO 17
<211> LENGTH: 24
<212> TYPE: DNA
<213> ORGANISM: Artificial Sequence
<220> FEATURE:
<223> OTHER INFORMATION: Primers

<400> SEQUENCE: 17
tagacgtcat atgaaggtgt gctt                                            24

<210> SEQ ID NO 18
<211> LENGTH: 25
<212> TYPE: DNA
```

```
<213> ORGANISM: Artificial Sequence
<220> FEATURE:
<223> OTHER INFORMATION: Primers

<400> SEQUENCE: 18
acgtcatatg aaggtgtgct tacaa                                          25

<210> SEQ ID NO 19
<211> LENGTH: 27
<212> TYPE: DNA
<213> ORGANISM: Artificial Sequence
<220> FEATURE:
<223> OTHER INFORMATION: Primers

<400> SEQUENCE: 19
ggatagacgt catatgaagg tgtgctt                                        27

<210> SEQ ID NO 20
<211> LENGTH: 27
<212> TYPE: DNA
<213> ORGANISM: Artificial Sequence
<220> FEATURE:
<223> OTHER INFORMATION: Primers

<400> SEQUENCE: 20
tggatagacg tcatatgaag gtgtgct                                        27

<210> SEQ ID NO 21
<211> LENGTH: 33
<212> TYPE: DNA
<213> ORGANISM: Artificial Sequence
<220> FEATURE:
<223> OTHER INFORMATION: Primers

<400> SEQUENCE: 21
tggatagacg tcatatgaag gtgtgctrac aag                                 33

<210> SEQ ID NO 22
<211> LENGTH: 27
<212> TYPE: DNA
<213> ORGANISM: Artificial Sequence
<220> FEATURE:
<223> OTHER INFORMATION: Primers

<400> SEQUENCE: 22
gaaaaatgat tatggctcag gtactgc                                        27

<210> SEQ ID NO 23
<211> LENGTH: 33
<212> TYPE: DNA
<213> ORGANISM: Artificial Sequence
<220> FEATURE:
<223> OTHER INFORMATION: Primers
<220> FEATURE:
<221> NAME/KEY: misc_feature
<222> LOCATION: (29)..(29)
<223> OTHER INFORMATION: n is u

<400> SEQUENCE: 23
gaaaaatgat tatggctcag gtactgcrna tcc                                 33

<210> SEQ ID NO 24
<211> LENGTH: 28
<212> TYPE: DNA
<213> ORGANISM: Artificial Sequence
<220> FEATURE:
<223> OTHER INFORMATION: Primers
```

```
<400> SEQUENCE: 24
tgaacgtggt caaatcaaag ttggtgaa                                          28

<210> SEQ ID NO 25
<211> LENGTH: 34
<212> TYPE: DNA
<213> ORGANISM: Artificial Sequence
<220> FEATURE:
<223> OTHER INFORMATION: Primers

<400> SEQUENCE: 25
tgaacgtggt caaatcaaag ttggtgaara gttg                                   34

<210> SEQ ID NO 26
<211> LENGTH: 28
<212> TYPE: DNA
<213> ORGANISM: Artificial Sequence
<220> FEATURE:
<223> OTHER INFORMATION: Primers

<400> SEQUENCE: 26
atttacggaa catttcaaca cctgtaac                                          28

<210> SEQ ID NO 27
<211> LENGTH: 34
<212> TYPE: DNA
<213> ORGANISM: Artificial Sequence
<220> FEATURE:
<223> OTHER INFORMATION: Primers

<400> SEQUENCE: 27
atttacggaa catttcaaca cctgtaacra gttg                                   34
```

METHODS OF ISOTHERMAL AMPLIFICATION USING BLOCKED PRIMERS

REFERENCE TO EARLIER FILED APPLICATION

This application is a continuation of PCT/US13/26202 filed Feb. 14, 2013, which claims the benefit under 35 U.S.C. §119(e) of U.S. Provisional Patent Application No. 61/598, 648, filed Feb. 14, 2012, and titled "RAPID DETECTION OF RPOB GENE MUTATIONS CONFERRING RIFAMPIN RESISTANCE IN MYCOBACTERIUM TUBERCULOSIS," which are incorporated, in their entirety, by this reference.

BACKGROUND OF THE INVENTION

The global incidence of drug resistant TB (*Mycobacterium tuberculosis*), particularly multi-drug resistant (MDR) and extremely-drug resistant (XDR) strains, is a major worldwide issue. Rates of MDR TB have been estimated to be 4.8% of the estimated 9.8 million TB infections, but rates as high as 55% have been observed for previously treated patients. TB can be effectively treated if properly identified. However, delayed initiation of appropriate treatment in suspected MDR-TB cases is associated with excess morbidity and nosocomial transmission.

It has been determined that the main contributor to delay in treatment is poor sensitivity of diagnostic tests; the average sensitivity of sputum microscopy is <60% in immunocompetent patients and is lower in HIV infected cases. Frequent smear-negative disease increases the difficulty with detecting HIV-associated TB as well. While mycobacterium culture is much more sensitive, it has a very slow turnaround time of 2-8 weeks and is technically complex. Nucleic acid amplification-based tests have improved detection sensitivity and time-to-result but historically have been difficult to effectively implement. A recently described real-time PCR approach brings ease-of-use but at high cost.

SUMMARY OF THE INVENTION

In one aspect, a method of isothermal, nucleic acid sequence amplification is disclosed. The method includes (a) mixing a target sequence with a blocked primer, wherein the blocked primer includes a flap comprising a single ribonucleotide at its 5' end and a blocking modification at its 3'-end such that extension by DNA polymerase cannot take place; (b) contacting the mixture of step (a) with a thermostable RNase H enzyme and thermostable helicase-dependent amplification reagents; (c) heating the mixture of step (b), wherein the RNase H enzyme removes the flap from the blocked primer resulting in an unblocked primer, and the helicase-dependent amplification reagents extend the unblocked primer to produce a double stranded amplicon which is denatured into a single stranded nucleic acid amplicon that can hybridize to a blocked primer.

In some embodiments, the RNase H enzyme is RNase H1. In some embodiments, the RNase H enzyme is RNase H2. In some embodiments the RNase H enzyme is present at a concentration of 1 mU/μL or greater. In some embodiments, the RNase H2 enzyme is present at a concentration of 3 mU/μL or greater.

In some embodiments, the blocked primer is of the formula: 5'-dNa-Nb-dNc-X-3', wherein a is an integer of 11 or more; b is an integer of 1; c is an integer of 1 or more; dN is a deoxyribonucleotide or nucleotide analog; N is an unmodified ribonucleotide or modified ribonucleotide; X is a deoxynucleotide, nucleotide, nucleotide analog, or nonnucleotide modification such that extension by DNA polymerase cannot take place. In some embodiments, the primer flap contributes greater than 2° C. to the melting temperature of the primer. In some embodiments, the primer flap consists of at least 3 base pairs and includes at least one cytosine or guanosine base. In some embodiments, the primer flap does not have a cytosine or guanosine base and consists of at least 4 base pairs. In some embodiments, the primer flap has no cytosine or guanosine and consists of at least 2 bases selected from a modified base and minor groove binder. In some embodiments, the primer flap is removed within about 15 minutes using a cleavage assay containing about 10 mU/μL of RNase H2, about 200 nM target sequence, and about 400 nM blocked primer incubated at 70° C.

In some embodiments, the amplicon is detectable in less than about 60 minutes. In some embodiments, the amplicon is detectable in less than about 30 minutes. In some embodiments, the HDA amplification reagents are selected from one or more of the group consisting of: buffer, DNA polymerase, helicase, single stranded binding protein and deoxynucleotide triphosphates. In some embodiments, the HDA amplification reagents include are selected from one or more of the group consisting of: buffer, DNA polymerase, single stranded binding protein and deoxynucleotide triphosphates.

BRIEF DESCRIPTION OF THE DRAWINGS

FIG. 3(*b*) shows an array map.

DETAILED DESCRIPTION

Figure 1:
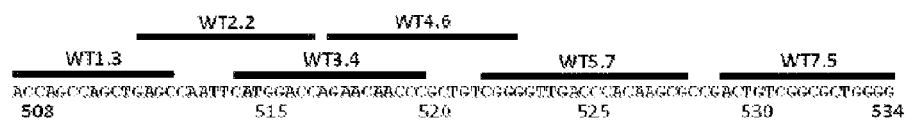
FIG. 1 shows an alignment of probes with the 81 base pair core sequence of the rpoB gene.

While the terminology used in this application is standard within the art, the following definitions of certain terms are provided to assure clarity.

Units, prefixes, and symbols may be denoted in their SI accepted form. Unless otherwise indicated, nucleic acids are written left to right in 5' to 3' orientation. Numeric ranges recited herein are inclusive of the numbers defining the range and include and are supportive of each integer within the defined range. Amino acids may be referred to herein by either their commonly known three letter symbols or by the one-letter symbols recommended by the IUPAC-IUBMB Nomenclature Commission. Nucleotides, likewise, may be referred to by their commonly accepted single-letter codes. Unless otherwise noted, the terms "a" or "an" are to be construed as meaning "at least one of." The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose. In the case of any amino acid or nucleic sequence discrepancy within the application, the figures control.

The term "nucleic acid" refers to double stranded or single stranded DNA, RNA, or DNA/RNA hybrids. Those molecules that are double stranded nucleic acids may be nicked or intact. The duplexes may be blunt ended or have single stranded tails. The single stranded molecules may have secondary structure in the form of hairpins or loops and stems. The nucleic acid may be isolated from a variety of sources including the environment, food, biological fluids such as blood, bronchial lavage or respiratory tract samples, sputum, nasal secretions, stool, swabs of mucosal tissues or tissue samples or cells. Nucleic acids may be obtained from cells including chromosomal DNA, plasmid DNA, recombinant DNA, DNA fragments, messenger RNA, transfer RNA, ribosomal RNA, and other RNAs such as siRNA that occur in cells. Any of these nucleic acids may be subject to modification where individual nucleotides are chemically altered. Modifications may be derived naturally, by in vitro synthesis, or by chemical modification. The term "duplex" refers to a nucleic acid that is double stranded in whole or part.

The term "target nucleic acid" or "target sequence" refers to a whole or part of nucleic acid to be selectively amplified and which is defined by 3' and 5' boundaries. The target nucleic acid may also be referred to as a fragment or sequence that is intended to be amplified.

The term "melting", "unwinding", or "denaturing" refer to separating all or part of two complementary strands of a nucleic acid duplex.

The term "hybridization" refers to binding of an oligonucleotide primer or probe to a region of single stranded nucleic acid template under the conditions in which the primer or probe binds to its complementary sequence on one of the template strands.

The term "primer" refers to a single stranded nucleic acid capable of binding to a single stranded region on a target nucleic acid to facilitate polymerase dependent replication of the target nucleic acid. The term "blocked primer" refers to a primer which has a modification at its 3'-end that prevents primer extension by DNA polymerase. The term "flap" in reference to a blocked primer refers to that portion of a primer that is downstream (in the 3' direction) of the primer from and including a ribonucleotide. For example, if the primer were defined by the formula 5'-dNa-Nb-dNc-X-3', where a is an integer of 11 or more; b is an integer of 1; c is an integer of 1 or more; dN is a deoxyribonucleotide or nucleotide analog; N is an unmodified ribonucleotide or modified ribonucleotide; X is a deoxynucleotide, nucleotide, nucleotide analog, or nonnucleotide modification such that extension by DNA polymerase cannot take place, then the Nb-dNc-X portion constitutes a primer flap.

The term "helicase" refers to any enzyme capable of unwinding a double stranded nucleic acid enzymatically. Helicases are enzymes that are found in all organisms and in all processes that involve nucleic acid such as recombination, replication, repair, transcription, translation, and RNA splicing (Kornberg and Baker. DNA Replication. W.H. Freeman and Company ($2^{nd}$ ed. (1992)). Any helicase that translocates along DNA or RNA in a 5' to 3' direction or the opposite 3' to 5' direction may be used, including for example, DnaB, PriA, PcrA, T4 Gp41 helicase, T4 Dda helicase, T7 Gp4 helicases, and thermostable UvrD helicase from *T. tengcongensis* and *T. thermophilus*.

The term "isothermal amplification" refers to amplification that occurs at a single temperature.

The term "primer dimer" or "primer artifact" refers to a target nucleic acid independent amplification product. This is thought to occur due to primer extensions wherein another primer serves as a template.

The term "thermostable" or "thermophilic" refers to an enzyme that has optimal activity at elevated temperatures and less activity at lower temperatures. Elevated temperature means greater than 50° C., but ideally about 65° C., in the case of RNase H2 from *Pyrococcus abyssi* and the uvrD helicase used in examples herein and lower temperature means less than 37° C. For the RNase H2 enzyme, the difference in activity between 25° C. and 65° C. is 10-fold or greater whereas the activity of uvrD helicase is 30% lower at 40° C. than at 55° C.

The term "hot start" describes a condition where the enzymes used in a nucleic acid amplification reaction are not substantially active until an elevated temperature is attained. This avoids activity at lower temperatures where primer dimers, primer artifacts, and primer misannealing to non-target regions of nucleic acids can create undesired amplification products. These amplification artifacts compete for the amplification of target sequences, lowering sensitivity and specificity of the amplification reaction.

The term "blocking group" refers to a chemical moiety that is bound to the primer or other oligonucleotide such that amplification does not occur. For example, primer extension does not occur. Once the blocking group is removed from the primer or other oligonucleotide, the primer is capable of participating in the assay disclosed herein, for example primer extension.

Ribonucleases (Rnases) are enzymes catalyzing hydrolysis of RNA into smaller components. The RNase H enzyme and its family of enzymes are endo-nucleases that catalyze cleavage of RNA of which there are two classes: RNase H1 and RNase H2. All of these enzymes share the characteristic that they are able to cleave the RNA component of an RNA:DNA heteroduplex or within a DNA:DNA duplex containing RNA bases within one or both of the strands. The cleaved product yields a free 3'-OH for both classes of RNase H. RNase H1 requires more than a single RNA base within an RNA:DNA duplex for optimal activity, whereas RNase H2 requires only a single RNA base in an RNA:DNA duplex.

The term "multiplex" refers to the amplification of multiple target nucleic acid sequences simultaneously. This involves the use of multiple pairs of primers present together in the amplification reaction.

The term "HDA amplification reagents" refers to one or more of the following reagents: buffer, DNA polymerase, helicase, single stranded binding protein, and deoxynucleotide triphosphates. In some embodiments, the HDA amplification reagents include buffer, DNA polymerase, single stranded binding protein, and deoxynucleotide triphosphates. In some embodiments, the HDA amplification reagents include buffer, DNA polymerase, helicase, and deoxynucleotide triphosphates To address the needs of bringing sensitive and specific diagnostic testing closer to the patient in the developing world, a simple, low cost approach for the specific detection of *M. tuberculosis* and mutations within the rpoB gene that confer resistance to the first line drug, rifampin are described and sometimes referred to as TB ID/R. Target DNA sequences within the rpoB gene are amplified using bpHDA which utilizes the isothermal amplification method helicase-dependent amplification to exponentially amplify target DNA sequences coupled with blocked primer/RNase H2 mediated target-specific "hot start." Resultant amplicons are detected by hybridization to a probe set arrayed onto a modified silicon chip surface that detects mutations in the rpoB gene amplified region such that intermolecular interactions trigger colorimetric intensity changes, permitting visual detection of attomole quantities of nucleic acids.

The isothermal techniques contemplated with this disclosure include a general means for isothermal amplification. As already mentioned, this means for isothermal amplification includes helicase-dependent amplification and thermophilic helicase-dependent (tHDA) amplification. Also, this isothermal amplification includes loop-mediated isothermal amplification of DNA (LAMP), reverse transcription polymerase chain reaction (RT-PCR), ligase chain reaction (LCR), transcription-based amplification systems (TAS), including nucleic acid sequence based amplification (NASBA), "Rolling Circle," "RACE" and "one-sided PCR." Embodiments disclosed herein should be considered representative and exemplary of a general class of isothermal amplification.

Capture Probe Design

A set of overlapping probes were designed covering the core region of the rpoB gene where the majority of mutations that confer rifampin resistance occur (FIG. 1). The rpoB gene of *Mycobacterium tuberculosis* (27, GenBank Accession #L27989). has an 81 base pair core sequence (including codons 508-534), which harbors the majority of clinically relevant mutations for reported drug-resistant tuberculosis cases. A 128 base pair fragment containing this core region was amplified using the innovations herein described. Probes hybrize to the indicated regions of the amplicon as shown in FIG. 1.

We designed the probe set to be matched to the wild-type rpoB gene sequence of *M. tuberculosis*. DNA capture probes were designed using MeltCalc™, which uses nearest neighbor calculations to optimize discrimination of all potential mutations. Criteria were set for a Tm of 58-60° C. under assay conditions of 825 mM monovalent cation. Higher melting temperature probes (68° C.) were required for those covering the 3'-end of the amplicon (probes 5.7 and 7.5), due to the presence of competing secondary structure in the amplicon. Each probe was screened to maximize discrimination (delta $T_m$) of the major rifampin resistance mutations that it was designed to detect.

Chip Production

Crystalline silicon wafers were coated with the polymer amino functional T-structure polydimethyl siloxane (TSPS, United Chemical Technologies, Bristol, Pa.) and cured at 150° C. for 24 hours. The TSPS coated wafer was further prepared by conventional means (see Zhong, X. B., R. Reynolds, J. R. Kidd, K. K. Kidd, R. Jenison, R. A. Marlar, and D. C. Ward. 2003. Single-nucleotide polymorphism genotyping on optical thin-film biosensor chips. Proc. Natl. Acad. Sci. 100: 11559-11564) to create an aldehyde functionalized surface, and stored at room temperature.

Probes were synthesized by Integrated DNA Technologies, Inc. (Coralville, Iowa). The 5'-end of the probes was modified with a reactive hydrazide group designed to interact and attach to the aldehyde-functionalized surface of the silicon wafers. Probes in spotting buffer (0.1M phosphate buffer pH 7.8, 10% glycerol) were printed (75 nanoliters) on the SFB coated silicon wafer using a BioDot Dispenser (model AD5000). A detection control (DC) is a biotin labeled probe spotted to control for the activity of the anti-biotin antibody/HRP conjugate and TMB performance. A hybridization control (HC) was also spotted that controls for the stringency of the hybridization step by reacting with a biotin-labeled complementary probe present in the hybridization buffer (antiC). After incubating for 2 hours, the wafers were washed with 0.1% SDS solution (sodium dodecyl sulfate in distilled, deionized water) dried and scribed into 6.5 mm² chips (DynaTek), and stored in nitrogen purged bags prior to use.

DNA Templates and Genomic DNA Samples

Single-stranded 128 base synthetic DNA templates covering the region of the rpoB gene were amplified using the TB ID/R assay. The wild-type and 28 mutant sequences were designed and synthesized by Integrated DNA Technologies. The mutated base within a probe is denoted by an uppercase letter, with wild-type bases in lowercase letters. The reference wild-type TB H37Ra genomic DNA template, other strains of non-cognate mycobacterium (NTM) species as well as other bacterial genera for the specificity test were provided by American Type Culture Collection (ATCC, Table 1). All other genomic DNA templates (from the wild-type and 26 mutant clinical isolates) were provided by ZeptoMetrix (Buffalo, N.Y.) and the detailed genotype information for those isolates is listed in Table 2.

Primers and Blocked Primer Helicase-Dependent Amplification (bpHDA)

Primers were designed against the wild-type sequence rpoB gene sequence of *Mycobacterium tuberculosis* using previously published parameters for HDA design (see An, L., W. Tang, T. A. Ranalli, H. J. Kim, J. Wytiaz, and H. Kong. 2005. Characterization of a thermostable UvrD helicase and its participation in helicase-dependent amplification. J. Biol. Chem. 280:28952-28958), with Primer 3 software. Due to the high GC content of the *M. tuberculosis* genome, constraints were relaxed for primer GC content, product Tm, and product length. The sequences of the blocked primers are rpoB1502F63 (SEQ ID NO: 1-5'-CGA TCA AGG AGT TCT TCG GCrA CCA G/iSpC3-3') and rpoB1629F52 (SEQ ID NO: 2-5'-/5BioTEG/GGC ACG CTC ACG TGA CAG ArCC GCC/iSpC3-3'), where iSpC3 indicates a C3 block at the 3'-end of the primer sequence. Unblocked primers sequences used were rpoB1502F1((SEQ ID NO: 3-5'-CGA TCA AGG AGT TCT TCG GC-3') and mtb-9R1 (SEQ ID NO: 4-5'-GGC ACG CTC ACG TGA CAG A-3'). All primers were synthesized by Integrated DNA Technologies, Inc.

Amplification reactions were performed at 65° C. using 1×ABII buffer (3.85 mM of MgSO4, 40 mM of NaCl, 0.4 mM of IsoAmp dNTPs), 1×IsoAmp Enzyme mixture (BioHelix), 10 mU/µL RNaseH2 (IDT), 0.01% Tween-20, 0.01% Triton X-100, 200 nM rpoB1502F63 and 400 nM rpoB1629F52. For real-time amplification, Eva green dye (Biotium, Inc.) was added to a final amount of 0.2× for each reaction and fluorescence was monitored using the LC 480 instrument (Roche). To determine amplification efficiency, the amount of input genomic DNA to the amplification reaction was plotted vs. crossing time (time of amplification required to generate detectable fluorescence signal) and fitted to a linear curve fit. The slope of the curve is used to calculate efficiency as follows: Efficiency=$10^{(-1/slope)}-1$.

The natural log of the amount of genomic DNA was plotted against the natural log of crossing time to determine the doubling rate (in minutes) as follows: ln(copies gDNA)=kt+ln(crossing time), where k=doubling time.

Chip Assay and Imaging

The assay was performed using chips immobilized in 96-well plates with flat, square bottom wells (Whatman). 20 µl of amplicon and 80 µl of hybridization buffer (5×SSC, 5 mg/mL alkaline treated casein, 0.05% Tween-20, and 0.03% ProClin-300 preservative, 250 pM biotin-labeled reverse complementary sequence for the hybridization control probe, (C) were added and briefly mixed in the well for each chip and then the plate was incubated for 6 minutes in an oven (Torrey Pines Scientific) set at 95° C. to denature the amplicon. After denaturation, the plate was immediately transferred into a second hybridization oven set at 53° C. for 10 minutes. After hybridization, the wells were then briefly washed 3 times (200 μl each) with wash buffer A (0.1×SSC, 0.1% SDS) followed by 3 times (200 μl each) with wash buffer B (0.1× SSC, 0.01% Tween 20). After wash, 100 μl of peroxidase-conjugated anti-biotin monoclonal mouse antibody (Jackson ImmunoResearch Laboratory, Inc) in 75 mM sodium citrate, 500 mM sodium chloride, 10% fetal bovine serum, 5 mg/ml alkaline treated casein, 0.5% ProClin300 preservative was added to the well and then incubated at room temperature for 10 minutes. The wells were further briefly washed 3 times (200 μl each) with wash buffer B at room temperature. Then, 100 μl of TMB substrate (BioFX/SurModics) was added and incubated at room temperature for 5 minutes. Finally, the wells were rinsed twice with distilled water and methanol, respectively. The chips were dried using compressed air and images were taken using a CCD camera controlled by μ Eye (IDS Imaging Development Systems GmbH Obersulm, Germany).

Chip Data Quantitative Analysis

ImageJ (National Institute of Health; imagej.nih.gov/ij/) was used to quantify the chip spot signal intensity. A circle was placed in the spot around the edge and the average signal pixel intensity was measured. The same circle was then dragged out to the neighboring non-spot area and the average pixel intensity was measured to generate background pixel value. The adjusted average spot signal intensity was obtained by subtracting the background from the reacted spot signal intensity. For each probe with signal intensity greater than 100 pixels, the result was determined to be wild-type. Those values were then averaged to determine a mean wild-type signal. Any probe signal less than 50 was determined to cover a mutant allele. Mean wild-type signal was divided by mutant signal to determine a signal-to-noise ratio for each mutation. For a result to be considered a valid test for the presence of the *M. tuberculosis* complex (TBC) at least three probes must have signal greater than 100 pixels within 2-fold of each other. A ratio of greater than 2 indicated the presence of a mutation.

rpoB Gene Re-Sequencing

A DNA sequencing template (440 bp) containing the rpoB amplicon region was PCR-amplified from 100 nanograms of genomic DNA using 500 nM primers (rpoB1375F, SEQ ID NO: 5-5'-CTGATCCAAAACCAGATCCG-3' and rpoB1814R, SEQ ID NO: 6-5'-TACAC-GATCTCGTCGCTAAC-3') in the Roche LightCycler 480 SYBR Green I Master kit and then gel-purified. The DNA templates were bi-directionally sequenced (SeqWright, Inc.) using the rpoB gene specific primers; rpoB1402F, SEQ ID NO. 7-5'-ATGTCGCGGATGGAGCGGGTG-3' and rpoB1721R, SEQ ID NO. 8-5'-GAGCCGATCAGACCGAT-GTTG-3'.

bpHDA Principle and Characterization

Figure 2:
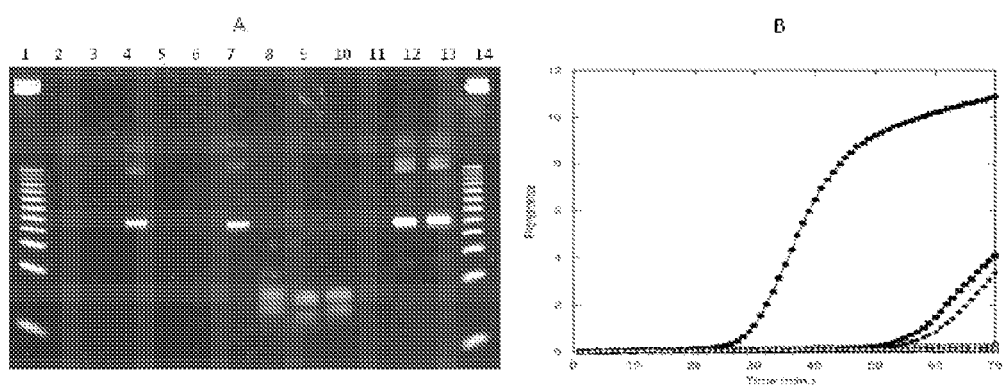
FIG. 2 shows (a) gel analysis of various amplicons and (b) real time amplification analysis of various assays.

Because the *M. tuberculosis* genome has a high GC content (65%; data available at tuberculist.epfl.ch/), primer artifact is a major potential competing side reaction in target amplification approaches, impacting assay sensitivity and the ability to multiplex. Initial designs using unmodified HDA primers were successful in amplifying genomic DNA using up to 50 nM primer concentration; at higher primer concentrations, only primer artifact was amplified. (See FIG. 2a). Referring to FIG. 2a, gel analysis of amplicons in 14 lanes is shown. Lanes 1 and 14 were for 25 base pair DNA ladder; lanes 2-4 were for 50 nM/50 nM unblocked HDA primers; lanes 5-7 were for 50 nM/50 nM pbHDA; lanes 8-10 were for 200 nM/400 nM unblocked HDA primers; lanes 11-13 were for 200 nM/400 nM bpHDA; lanes 2, 5, 8, 11 had no template control; lanes 3, 6, 9, and 12 had 30 copies input H37a genomic DNA from *M. tuberculosis*; lanes 4, 7, 10, and 13 had 30,000 copies H37a genomic DNA.

Under these conditions, amplification reactions were slow, requiring 60.3 minutes to get detectable signal for 30,000 copies of genomic DNA in real-time amplification experiments. (See FIG. 2b). Referring to FIG. 2b, real time amplification observations were recorded: the closed circle was for 200 nM/400 nM bpHDA; closed square was for 50 nM/50 nM bpHDA; closed diamond was for 50 nM/50 nM unblocked HDA primers; open circle was for 200 nM/400 nM bpHDA; open square was for 50 nM/50 nM bpHDA; open diamond was for 50 nM/50 nM unblocked HDA primers. All open symbols in the graph of FIG. 2b contained no template controls, and all close symbols contained 30,000 H37a genomic DNA. From these results, it appeared that sensitivity was poor with the inability to amplify genomic DNA amounts below 100 copies even after 90 minutes reaction time. Because organism load may be low in respiratory tuberculosis sputum samples, these primers were deemed unacceptable for use on clinical specimens.

To overcome these problems, we utilized modified blocked primers constructed with a single ribonucleotide linkage 4 bases upstream of a 3'-end block, to prevent primer extension. Once blocked primers hybridize to complementary target sequences, thermostable RNase H2 derived from *Pyrococcus abyssi* is activated, cleaving the ribonucleotide linkage in the primer present in duplex DNA. The short segment of the primer 3' of the ribonucleotide dissociates, liberating the flap which blocks amplification, creating a free 3'-hydroxyl which is now capable of primer extension. RNase H2 used here has very little activity at temperatures below 40° C. and is highly active at 65° C., the temperature required for HDA to amplify target sequences optimally. Because primer/primer hybrids are unstable at elevated temperatures, it is believed that primer artifact is not amplified.

In experiments with wild-type *M. tuberculosis* genomic DNA, amplification using blocked primers at the same concentration as the unblocked primers displays similar kinetic behavior; the time required to get detectable amplification product was roughly the same (FIG. 2b). With the blocked primer approach, however, higher concentrations may be used to amplify target DNA (FIG. 2a). Therefore, the amplification reactions are more rapid with a crossing time of 29.7 minutes versus 57.1 minutes at lower primer concentration.

Additionally, the ability to amplify low amounts of genomic DNA is possible, with amplification of 1 copy detectable by real-time analysis within 50 minutes. Speed and efficiency of the blocked primer approach was measured by amplifying various known quantities of wild-type genomic DNA in a real time detection instrument. Plotting of genomic DNA amounts versus crossing time reveals a highly efficient exponential amplification system (95-100%), with a rapid doubling time of 78 seconds. Even after letting the amplification reaction sit at room temperature of 30 minutes, no primer artifact was generated using blocked primers, further confirming that the RNase H2 must be at elevated temperatures to become active.

TB ID/R Analytical Performance

To detect mutations present within the region of the rpoB gene amplified here, we created a set of overlapping probes with perfect complementary to wild-type *Mycobacterium tuberculosis*, arrayed onto a modified silicon chip. If a mutation is present in the amplicon, hybridization signal will be dramatically reduced or eliminated for the probe that is complementary to the mutated region. For those mutations that are covered with two overlapping probes, both probes could be affected. (See FIG. 1).

To validate sensitivity and specificity of the final array, a set of full-length, single-stranded templates was designed representing >95% of all known mutations in the rpoB core sequence of M. tuberculosis. Each was tested with the TB ID/R assay and each chip image was captured using a CCD camera.

Figure 3:
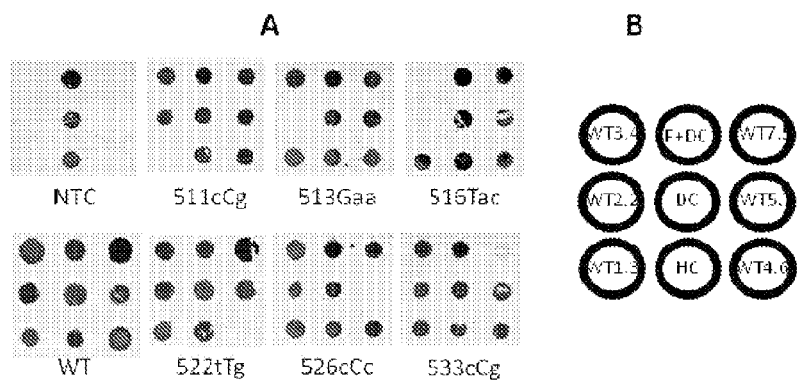
FIG. 3 shows SNP discrimination within the rpoB gene of *Mycobacterium tuberculosis* using the TB ID/R technique described herein and specifically FIG. 3(*a*) shows images of mutations that affect each probe.

FIG. 3 shows rpoB gene discrimination using TB ID/R. Synthetic 128 base pair templates were amplified using bpHDA ad described, then hybridized to a chip, and a CCD camera image was captured. As shown in FIG. 3(a), probe signals were visually unambiguous; the wild-type amplicon displayed clear and balanced signal for all probes. For the target sequences with mutations in codons 509 to 531, complete loss of signal was observed in the probes that cover the mutant allele. Significant, but not complete, reduction in signal was observed for the various mutations in the 533 codon. For all of the tested point mutations, a single probe lost signal except in the case of mutations within codons 516 and 518 which affected the two probes that overlap those alleles. One mutation, 508Gcc, could not be discriminated with this probe set. An array map is shown in FIG. 3(b) where HC represents hybridization control; DC represents detection control, and F+DC represents fiducial marker mixed with detect control.

Figure 4:
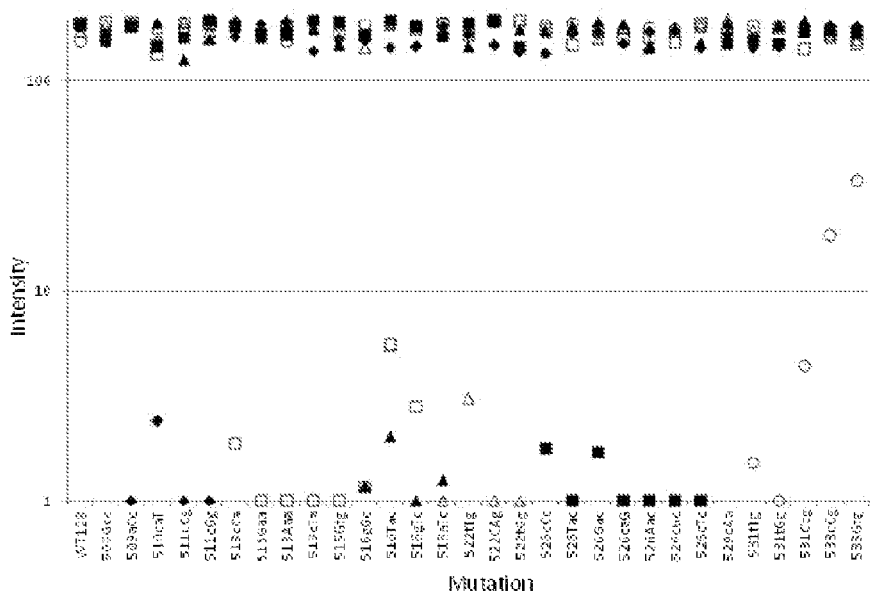
FIG. 4 shows the performance of the TB ID/R technique described herein and signals for each probe detected.

Due to the virtually binary response of the probes to mutations, visual discrimination is straightforward: if a spot is missing or very faintly present then a mutation is present. However, the array is still visually complex so image analysis was also investigated to generate an automated call. Probe pixel intensities were determined from the CCD image, corrected for background, and plotted for each tested sample. (See FIG. 4). Referring to FIG. 4, synthetic templates with mutation indicated by uppercase letter were amplified, tested by TB ID/R, subject to CCD imaging, and image analysis as described and shown. Signals for each probe on each chip were plotted as follows: probe WT1.3 (closed diamond); probe WT2.2 (open square); probe 3.5 (closed triangle); probe WT4.6 (open triangle); probe WT5.7 (closed square); probe 7.5 (open circle). Signals below 10 pixels are difficult to detect by the unaided eye. CCD image analysis verified the visual interpretation of the assay performance All tested mutations except in codon 533 have signal drop-out (less than 10 pixels). Analysis of each mutant sample reveals signal-to-noise ratio of greater than 20 for the drop-outs, 5.2 for 533Gtg and 9.4 for 533cCg allowing for unambiguous discrimination.

Figure 5:
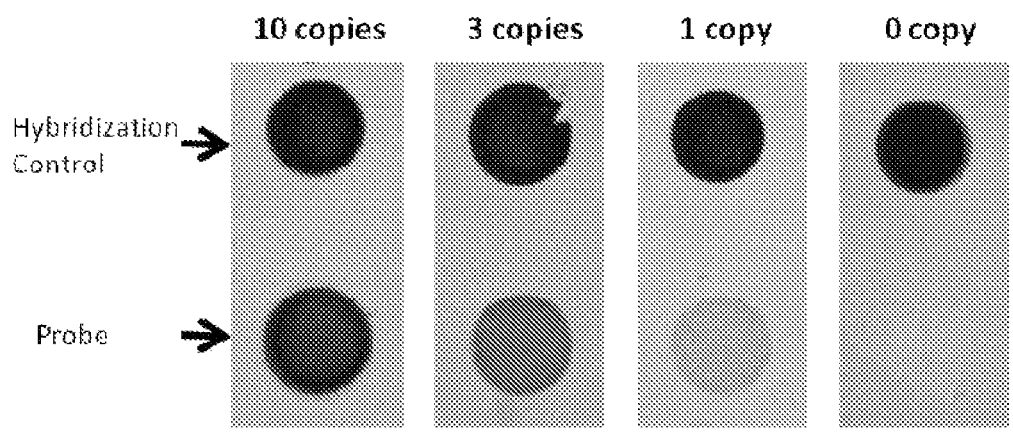
FIG. 5 shows the TB ID/R assay limit of detection (LOD).

A limit of detection was determined by titrating known quantities of purified, wild-type MTB genomic DNA using the TB ID/R assay. To detect a single copy of genomic DNA, 40 minutes of amplification time was required. (See FIG. 5). Referring to FIG. 5, the assay limit of detection (LOD) was determined using wild type (H37Ra) genomic template with an amplification time of 40 minutes. The top row shows the hybridization control for assay performance. The bottom row indicates signal from one probe (WT1.3) as a function of input copy number of genomic DNA to the TB ID/R assay.

Additionally, we determined reactivity with other mycobacterium species including within the TB complex (Table 1). All members of the TB complex tested including M. bovis, M. microti, and two strains of M. africanium generated signal on all probes. Using the criteria that at least three probes must have signal >100 and within 2-fold of each other, none of the 5 NTM species were detected. However, M. genavense yielded strong signal on two probes and very weak signal on another. Testing of several non-mycobacterium genomic DNA samples, including human DNA, displayed no signal (see Table 1).

Clinical Isolate Testing

To further verify this assay, we tested genomic DNA from clinical isolates for 10 wild-type and 26 RIF-resistant specimens. TB ID/R assay correctly classified 10/10 wild-type samples (100% specific, 95% CI 65.6-100%) and 24/26 RIF-resistant samples (92.3%, 95% CI 73.4-98.7%) compared to rpoB gene sequencing. The wild-type amplicons displayed strong signal on each probe with less than 2-fold variability across 10 unique isolates (data not shown). For each of the clinical samples containing a single mutation, similar levels of discrimination as compared to results obtained using synthetic templates were observed. Signal drop-out was observed for mutations in codons 511 to 526. Discrimination was not as good for the amplicon from genomic DNA for the S531L mutation as for the synthetic template but was easily discriminated with signal-to-noise ratio of 19 as an average for three unique strains. The L533P mutation performed similarly to the synthetic template with signal-to-noise of 5.3. Two samples, correctly classified as mutant by TB ID/R, were determined to harbor a single mutant allele by rpoB gene sequencing, however each had evidence of more than one mutation present by TB ID/R. Sample #8094, which was originally reported to be a single D516G mutation, had signal loss in probes 1.3, 2.2, and 3.4 indicating an additional mutation in an upstream codon. Re-sequencing of the rpoB gene revealed a mutation in 511 cCg, which explains the loss of signal in probe 1.3. Sample #11230 was reported to be a sample with a single mutation at H526N. TB ID/R detected this sample as containing a mutation, but with a very low ratio, 2.6. Re-sequencing of this sample revealed a mixed base at the mutant position indicating the presence of two unique alleles present, explaining the low ratio for this mutation. The TB ID/R assay was further challenged with 6 samples with multiple mutations in the rpoB core region. TB ID/R correctly classified 5/6 as mutant, but with unexpected probe response in some cases. Sample #18740 with three mutations (S512R/Q513P/D516A), which should have been detected by signal loss in probes 1.3, 2.2, and 3.4, was detected by signal loss in probes 1.3 and 7.5 by TB ID/R. Re-sequencing of the rpoB gene confirmed the presence of a S512R mutation and additionally detected a 531tGg mutation, however both the Q513P and D516A mutations were not detected, concordant with the TB ID/R results. In the case of a sample with H526N/L533V (#15606), signal was lost only with probe 7.5, when both probe 5.7 and 7.5 should have lost signal.

Two samples that were discordant between the TB ID/R assay and the initial rpoB gene sequencing were subject to repeat sequencing of the rpoB gene. Sample #16866 was mis-identified as wild-type by TB ID/R. Re-sequencing confirmed the initial sequencing determination for the sample to be a mixed WT/H526Y result. Another sample (#8545) reported to contain a Q513P mutation by sequencing, was determined to be wild-type in the TB ID/R assay. Re-sequencing of the sample revealed no mutation at the 513 codon, concordant with the TB ID/R assay.

In one aspect, the amplification method includes a hot start component to the isothermal amplification method, HDA, which permits more rapid amplification and multiplexing. By using this blocked primer approach, initiation of DNA amplification is DNA target-dependent, improving sensitivity and specificity by mitigation of competing primer artifact amplification. Analysis revealed a highly efficient exponential amplification system with rapid doubling times suggesting initiation of HDA by RNase H2 mediated cleavage of blocked primers is rapid and not rate limiting. Amplified products were detected using a silicon chip modified with a polymer coating to create a surface with optical properties such that the surface-bound DNA hybrids transduce a permanent change in color intensity on the chip surface visible to the unaided eye. Additionally, the surface is molecularly flat and chemically inert, thereby reducing non-specific interactions allowing for highly sensitive and specific detection. This allows for discrimination of SNPs as demonstrated herein, and with picomolar limits of detection. Only short hybridization reactions are required with bpHDA amplified target sequences to generate detectable surface-bound hybrids. Because the signal response to mutations is effectively binary, results can be determined using either a non-instrumented visual approach or with an inexpensive CCD or CMOS camera-based imaging system.

The analytical performance of TB ID/R is similar to other recently described molecular methods for the detection of the *M. tuberculosis* complex strains including those with mutations in the rpoB gene associated with RIF resistance. A comprehensive set of mutant templates was constructed, and all mutations tested herein were discriminated with the exception of one, 508Gcc. Nearest neighbor analysis revealed that this probe set was unable to discriminate this mutation (delta $T_m=0°$ C.). This is a very rare mutation, accounting for less than 0.1% of the reported rifampin resistance cases in TB. Testing of genomic DNA isolated from clinical specimens displayed excellent sensitivity for the detection of RIF-resistant strains and specificity for RIF-sensitive strains. Re-sequencing of the two discrepant samples resolved one result in favor of TB ID/R, improving sensitivity to 96.2%. While it has been reported that identifying mutations in the core region of the rpoB gene is commonly sufficient to diagnose MDR TB (resistance to both rifampin and isoniazid (INH)), additional drug resistance information for rapid diagnosis of XDR TB (resistant to RIF, INH, fluroquinolones (FQ) and any one second-line aminoglycoside drugs such as kanamycin, amikacin, or capreomycin) would aid in appropriate management and treatment of even more infected patients, further reducing transmission risk. Unlike other recently described molecular diagnostic methods such as real-time PCR and LAMP with limited multiplex detection capabilities, resistance information can be readily added to the TB ID/R assay for detecting mutations in gyrA and gyrB genes for FQ resistance and the rrs gene for resistance to aminoglycosides. These markers have been shown to detect drug resistance with high sensitivity using another scalable test platform, reverse line blot hybridization assay (RLBH). However, the RLBH test is time-consuming and technically complex, limiting its usefulness in the point of care setting.

Multiple mutations within a sample, presumably from infections containing more than one TB strain or from individual strains with multiple mutations, present potential challenges for genotypic detection approaches. If two or more mutations exist within a single TB isolate, they are straightforward to detect, but if there is a mixture of multiple unique RIF-resistant strains or mixtures of both RIF-resistant and RIF-sensitive populations, resistance detection could be complicated. To illustrate this point, we tested two isolates that had a mixture of wild-type and mutant genomic templates (H526R/WT and H526Y/WT) and obtained very different results. Both the H526R and H526Y mutations create a signal drop-out for probe #5.7 in an isolate with a single mutation and thus, are strongly discriminated. We detected the H526R/WT sample unambiguously indicating the assay is tolerant to the presence of some amount of competing wild-type allele. However, the detection of the H526Y/WT as a wild-type sample by TB ID/R, suggests that if the ratio of the wild-type allele is higher, the potential for missing a mutation exists. Similarly, sample #15606 was correctly identified as a mutant sample, but not all of the mutations were detected suggesting the source of the mutations was from more than one infecting organism. In the case of the two samples with D516G/L533P mutants we were able to detect each mutation with the same level of discrimination as if they were singly mutated isolates, suggesting that they both occurred in the same organism. It has previously been observed in an assay with similar probe design, that the strength of discrimination of a given mutation has a strong effect on the ability to detect mutations in a mixed sample. This factor, combined with the fraction of each allele present, is critical for correct detection in RIF-resistant samples containing more than one infecting organism.

The need for improved point-of-care testing for drug resistance in *M. tuberculosis* is acute. Increasing the initial test sensitivity from 35% (microscopy sensitivity for HIV positive patient) to 95% (molecular diagnostic approaches) would decrease the mean delay in diagnosis by approximately 25 days and reduce the drop-out rate (infected individuals who cease seeking medical treatment) by approximately 30%. By providing drug resistance information during the initial diagnostic test, the delay in appropriateness of treatment, a critical factor in reducing attributable mortality for infectious diseases, would further be reduced. To address the need for an easy-to-use, highly sensitive diagnostic test for *M. tuberculosis* identification and drug susceptibility information, the TB ID/R test may be conducted using a disposable cartridge executed on a small, inexpensive, electromechanically simple, and potentially battery-powered device. Automation of this test may also be accomplished. The combination of isothermal amplification with chip-based, eye visible detection allows for the use of low cost heaters and imaging equipment. Additionally, low cost, highly stable and robust reagents, with measured stability at 37° C. of 9 months so far with no loss in activity (data not shown) is attainable. These reagents have been used in commercially successful assays performed in the point-of-care setting for test-and-treat indications such as viral and respiratory pathogens that require rapid, accurate results. Furthermore, the chips can be produced on very large scale inexpensively utilizing well-established semi-conductor processes.

The techniques described herein may also be used for identifying staphylococcal species and the presence of the mecA gene in gram positive cocci in cluster positive blood cultures from hospitalized patients. A low cost, easy-to-use device that can detect RIF resistance could have a tremendous impact on reducing community spread of the disease as well as improved outcomes for infected patients by providing appropriate treatment sooner.

EXAMPLES

Effect of RNase H2 Concentration on bpHDA Performance

Method: A triplex bpHDA was set up using a final concentration of 1×ABII buffer, 3.85 mM $MgSO_4$, 40 mM NaCl, 0.4 mM dNTP mixture, 0.01% Tween-20, 0.01% Triton X-100, 5 ng/μL uvrD helicase, 2 ng/μL single stranded binding protein, and 0.8 ng/μL GST DNA polymerase (BioHelix, Beverly, Mass.) containing 200 nM each blocked primers mecA898-ribo, mec990r-bio-ribo, tuf4301-bio-ribo, tuf527r-bio-ribo, nuc555f-bio-ribo, and nuc661r-ribo. RNase H2 (IdT Technologies) was added to final concentrations of 100, 31.6, 10, 3.16, 1 and 0 mU/μL. A 2× enzyme mix was created and added to individual wells of a microtiter plate. Methicillin-resistant *Staphylococcus aureus* (ATCC 33592) spiked positive blood Cx (BACTEC, BD) were extracted using an achromopeptidase-based extraction buffer, primers were added to extracted cells to produce a 2× template/primer mix, which was then added to the 2× enzyme mix and incubated at 65° C. The reaction was monitored (LC480, Roche) via binding of the dye EvaGreen to double stranded DNA that is formed during amplification.

Result: As is seen in Table 1, no amplification occurred within 45 min at 1 mU/µL RN2, and significant rate increase was observed up to 31.6 mU/µL RN2. This result contrasts with the observation that a PCR reaction is equally efficient for blocked and unblocked primers using 0.1 mU/µL RNase H2 (Dobosy et al). In the case of bpHDA, RN2 cleavage was demonstrated to be rate-limiting up to 100 mU/µL, or 380-fold greater RN2 concentration than was used in the PCR conditions.

TABLE 1

Effect of RNase H2 amount on bpHDA performance

| [RNase H2] | Crossing time (mean +/− SD) |
|---|---|
| 0 | >45 |
| 1 mU/µL | >45 |
| 3.2 mU/µL | 33.8 +/− 6.4 |
| 10 mU/µL | 20.5 +/− 0.8 |
| 32 mU/µL | 12.9 +/− 0.4 |
| 100 mU/µL | 11.3 +/− 0.4 |

Comparison of Amplification Rates for HDA versus bpHDA

Method: Reactions were set-up using a final concentration of 1×ABII buffer, 3.85 mM MgSO$_4$, 40 mM NaCl, 0.4 mM dNTP mixture, 0.01% Tween-20, 0.01% Triton X-100, 5 ng/µL uvrD helicase, 2 ng/µL single stranded binding protein, and 0.8 ng/µL GST DNA polymerase (BioHelix, Beverly, Mass.) containing various concentrations of either blocked (tcdB7011f-RIBO/tedB7089r-RIBO) DNA primers for bpHDA amplifications or unblocked (tcdB7011f/tcdB7089r) DNA primers for HDA amplifications as indicated below (Tables 2-3). RNase H2 (IdT Technologies) was added to final concentrations of 30 mU/µL for the bpHDA reactions. A 2× enzyme mix was created and added to individual wells of a microtiter plate. To each well either water (no template control) was added or 100 copies of *Clostridium difficile* strain 630 genomic DNA (ATCC #BAA-1382D-5) and incubated at 65° C. The reaction was monitored (LC480, Roche) via binding of the dye EvaGreen to double stranded DNA that is formed during amplification.

Results and Conclusions: As is observed in Table 3, under all primer concentrations tested, the bpHDA approach (blocked) amplified genomic DNA from toxigenic *C. difficile* significantly faster than the HDA (unblocked) approach. Additionally, whereas the bpHDA amplification of 100 copies of input genomic DNA yielded a clean tcdB amplicon product, several of the HDA amplification reactions also contained amplified primer artifact. While amplification products from no template control (primer artifacts) showed shorter crossing times both for bpHDA and HDA with increasing primer concentration, in the case of HDA, primer artifact amplification crossing times (Ct) were approaching those of amplification of 100 copies of genomic DNA by 300 nM primer concentration, indicating a strong potential for competition during amplification which will negatively affect limit of detection. This impact on limit of detection will be more apparent at higher primer concentrations.

TABLE 3

Comparison of amplification results for blocked and unblocked primers

| primer type | Concentration (nM) | 100 copies [1]Ct | [2]AUC tcdB | AUC artifact | [3]NTC Ct |
|---|---|---|---|---|---|
| blocked | 300 nM each | 14.4 | 23.7 +/− 0.3 | none | 42.2 |
| blocked | 200 nM each | 17.2 | 19.7 +/− 0.2 | none | 45.0 |
| blocked | 100 nM each | 25.8 | 9.0 +/− 0.2 | none | >50 |
| unblocked | 300 nM each | 22.2 | 8.4 +/− 7.7 | 7.6 +/− 6.4 | 24.0 |
| unblocked | 200 nM each | 29.7 | 6.3 +/− 0.4 | none | 35.1 |
| unblocked | 100 nM each | 45 | 1 +/− 0.7 | 0.5 +/− 0.3 | >50 |

[1]Ct is equal to the number of minutes to cross detection threshold
[2]Area under the curve of the amplified product from the 100 copies of input genomic DNA.
[3]No template control reactions Effect of Flap Tm on bpHDA Amplification Rates Method: Reactions were set-up using a final concentration of 1×ABII buffer, 3.85 mM MgSO$_4$, 40 mM NaCl, 0.4 mM dNTP mixture, 0.01% Tween-20, 0.01% Triton X-100, 5 ng/µL uvrD helicase, 2 ng/µL single stranded binding protein, and 0.8 ng/µL GST DNA polymerase (BioHelix, Beverly, Mass.) containing various concentrations of blocked DNA primers for bpHDA amplifications (Tables 1-2). RNase H2 (IdT Technologies) was added to final concentrations of 3 mU/µL or 30 mU/µL. A 2× enzyme mix was created and added to individual wells of a microtiter plate. To each well either water (no template control) was added or 10,000 copies of *Clostridium difficile* strain 630 genomic DNA (ATCC #BAA-1382D-5) and incubated at 65° C. The reaction was monitored (LC480, Roche) via binding of the dye EvaGreen to double stranded DNA that is formed during amplification.

TABLE 2

Primers used in this study

| Name | IDT # | sequence |
|---|---|---|
| tcdB7011f-RIBO | 53492957 | SEQ ID NO.: 9 - TACAGATGAATATATTGCAGCAACTGrGTTCA/3SpC3/ |
| tcdB7089r-RIBO | 53492956 | SEQ ID NO: 10 - TTGAGCTGTATCAGGATCAAAATAATACTCrCTCAC/3SpC3/ |
| tcdB7011f | 42566931 | SEQ ID NO: 11 - TACAGATGAATATATTGCAGCAACTG |
| tcdB7089r | 42598201 | SEQ ID NO: 12 - TTGAGCTGTATCAGGATCAAAATAATACTC |

TABLE 4

Characteristics of primers used in this study

| Primer | Sequence | Tm with flap[1] | Tm w/o flap[1] | delta Tm (flap-no flap) |
|---|---|---|---|---|
| tcdB7012f-RIBO | SEQ ID NO: 13 - ACAGATGAATATATTGCAGCAACT GGTTCAgTTATT/3SpC3/ | 69.6 | 68.1 | 1.5 |
| tcdB7011f-RIBO | SEQ ID NO: 14 - TACAGATGAATATATTGCAGCAAC TGgTTCA/3SpC3/ | 67.8 | 63.1 | 4.7 |
| tcdB7089r-RIBO | SEQ ID NO: 15 - TTGAGCTGTATCAGGATCAAAATA ATACTCcTCAC/3SpC3/ | 68.5 | 64.7 | 3.8 |

[1]Primer Tms were measured using nearest neighbor thermodynamic calculations (Oligo Analayzer, www.idtdna.com), set at 60 mM NaCl and 4 mM MgSO4, and 0.25 µM oligo.

TABLE 5

Primer pairs used in this study

| Primer Pair | Fwd | Rev |
|---|---|---|
| 3b | tcdB7012f-RIBO | tcdB7089r-B-RIBO |
| 6b | tcdB7011f-RIBO | tcdB7089r-B-RIBO |

Results and Conclusions: As is seen in Table 6, both primer mix 3 and primer mix 6 have very similar amplification rates at 30 mU/µL of RNase H2. At 3 mU/µL of RNase H2, bpHDA amplification using primer mix 6 is only ~10% slower whereas primer mix 3 amplifies ~70% slower. The contribution of the flap to primer Tm is higher for the tcdB7011f-RIBO primer used within primer mix 6, confirming the strong effect of flap stability on bpHDA performance.

TABLE 6

Effect of primer mix and RNase H2 amount on bpHDA amplification rate

| Primer Mix | Primer Concentration (nM) | 30 mU/µl RN2 10K copies-Ct | 3 mU/µl RN2 10K copies-Ct | 30 mU/µl RN2 NTC-Ct | 3 mU/µl RN2 NTC-Ct |
|---|---|---|---|---|---|
| PM3 | 200 | 9.3 | 14.6 | 33.7 | 32.3 |
| PM3 | 100 | 11.6 | 18.9 | 42.1 | 42.0 |
| PM3 | 50 | 18.6 | 30.6 | >50 | >50 |
| PM6 | 200 | 8.9 | 10.3 | 34 | 34.6 |
| PM6 | 100 | 12.1 | 13.8 | 42.2 | 42.1 |
| PM6 | 50 | 18.0 | 20.9 | >50 | >50 |

Ct = minutes of bpHDA required to cross detection threshold
NTC = no template control Effect of RNase H2 Cleavage Rate and Flap Stability on bpHDA Performance Method: To determine RNase H2 cleavage rate of the various blocked primer, quenched/fluorescent primers were annealed to a synthetic DNA template (400 nM primer and 200 nM template), in RNase Mix (1× Annealing Buffer II, 3.85 mM MgSO4, 40 mM NaCl, 5% Ficoll 400 (Sigma), 7.5% Ficoll 70 (Sigma), 5% sucrose (Sigma), 0.01% Tween-20 (Sigma), 2.5 mg/mL bovine serum album (Probumin, Calbiochem), 0.01% Triton X-100 (Sigma) and 10 mU/µL Pyrococcus abyssi RNaseH2 (Integrated DNA Technologies) and incubated at 70° C. T1/2 for cleavage was the time required to achieve half-maximal cleavage as monitored by fluorescence change for fluorescein or HEX dyes using a Roche LightCycler480. Primer Tms were measured using nearest neighbor thermodynamic calculations (Oligo Analayzer, www. idtdna.com), set at 60 mM NaCl and 4 mM MgSO4, and 0.25 µM oligo. bpHDA reactions were set-up using a final concentration of 1×ABII buffer, 3.85 mM MgSO4, 40 mM NaCl, 0.4 mM dNTP mixture, 0.01% Tween-20, 0.01% Triton X-100, 5 ng/µL uvrD helicase, 2 ng/µL single stranded binding protein, 0.8 ng/µL GST DNA polymerase (BioHelix, Beverly, Mass.), 100 nM of forward mecA primer (Table 7), 200 nM reverse primer (mec990-bio-r2, used in all amplification reactions), and 10 mU/µL of RNase H2 was used in each amplification reaction.

Results: RN2 cleavage rate is proportional to the delta Tm between the cleaved and uncleaved primers; the greater the contribution of the flap to primer Tm the faster the cleavage by RNase H2. This indicates that flap stability is a critical component of RN2 cleavage rate. In turn, HDA rate is proportional to RN2 cleavage rate; the faster the cleavage of the blocked primer, the faster the amplification by bpHDA.

TABLE 7

Relationship of blocked primer cleavage rate and bpHDA amplification rate

| Primer | Label | Sequence | Flap | Tm | Tm with flap | T¹/₂, RN2 cleavage | Cp, HDA |
|---|---|---|---|---|---|---|---|
| mec899QF | FAM | SEQ ID NO: 16 - uACAA GGATAGACGTCATA TGAAGGTGTGCT | uACAA | 67 | 68 | 15' | >60' |
| mec902QF2 | FAM | SEQ ID NO: 17 - aCAAGT TAGACGTCATATGA AGGTGTGCTT | aCAAGT | 65 | 69 | 6' | 40' |

TABLE 7-continued

Relationship of blocked primer cleavage rate and bpHDA amplification rate

| Primer | Label | Sequence | Flap | Tm | Tm with flap | T½, RN2 cleavage | Cp, HDA |
|---|---|---|---|---|---|---|---|
| mecA905QF | FAM | SEQ ID NO: 18 - gTGCT ACGTCATATGAAGG TGTGCTTACAA | | 66 | 71 | <1' | 15' |
| Mec898BP10HEX | HEX | SEQ ID NO: 19 - aCAAG GGATAGACGTCATA TGAAGGTGTGCTT | | 68 | 70 | 8' | 42' |

Cp = minutes of bpHDA required to cross detection threshold
Note:
Each 3'-end was blocked using the label in column 2 of table 7.

TABLE 8

List of Strains For The Specificity Testing

| Strain | Source | Hybridization |
|---|---|---|
| Mycobacterium bovis-BCG | ATCC-#19015 | Wildtype |
| Mycobacterium microti | ATCC-#11152 | Wildtype |
| Mycobacterium africanum | ATCC-#35711 | Wildtype |
| Mycobacterium africanum | ATCC-#25420 | Wildtype |
| Mycobacterium abscesus | ATCC-#19977 | Negative for TB |
| Mycobacterium fortuitum | ATCC-#35754 | Negative for TB |
| Mycobacterium genavense | ATCC-#51234 | Negative for TB |
| Mycobacterium chelonae | ATCC-#35749 | Negative for TB |
| Mycobacterium celatum | ATCC-#51131 | Negative for TB |
| Clostridium difficile | ATCC-#BAA-1382D-5 | Negative for TB |
| Bacillus subtilis | ATCC-#23857D-5 | Negative for TB |
| Staphylococcus aureus (MRSA) | ATCC-#1005-22-03 | Negative for TB |
| Staphylococcus aureus (MSSA) | ATCC-#3555D-5 | Negative for TB |
| Homo sapiens | Roche (cat#-11691112001) | Negative for TB |
| S. Accromyces cerevisiae | Novagen (cat#-69240-3) | Negative for TB |

The effect of blocked primers on the ability to multiplex HDA reactions was examined Duplex amplification reactions were set up using a final concentration of 1×ABII buffer, 3.85 mM MgSO4, 40 mM NaCl, 0.4 mM dNTP mixture, 0.01% Tween-20, 0.01% Triton X-100, 5 ng/μL uvrD helicase, 2 ng/μL single stranded binding protein, and 0.8 ng/μL GST DNA polymerase (BioHelix, Beverly, Mass.) containing 200 nM each of blocked primers (mecA898-ribo, mecA990r-bio-ribo, tuf430L-bio-ribo, and tuf527r-bio-ribo) for bpHDA and 100 nM each of unblocked primers (mecA898f, mecA990r, tuf430L, and tuf527r) for standard HDA. RNase H2 (IdT Technologies) was added to final concentrations of 10 mU/μL for bpHDA reactions. A 2× enzyme mix was created and added to individual wells of a microtiter plate. Methicillin-resistant Staphylococcus aureus (ATCC 33592), methicillin-resistant Staphylococcus epidermidis (ATCC 700562, MRSepi), or methicillin-sensitive Staphylococcus warneri (ATCC 27836, S. warneri) spiked positive blood Cx (BACTEC, BD) were extracted using an achromopeptidase-based extraction buffer, primers were added to extracted cells to produce a 2× template/primer mix, which was then added to the 2× enzyme mix and incubated at 65° C. The reaction product was run on a 2% agarose gel stained with ethidium bromide. This results demonstrates the benefit of the bpHDA approach for simultaneous amplification of multiple nucleic acid target sequences due to the increase in specificity of the approach compared to standard HDA. Primer sequences identified in Table 9 below were used.

TABLE 9

Primers

| | | |
|---|---|---|
| mecA898f | SEQ ID NO: 20 - | 5'-TGGATAGACGTCATATGA AGGTGTGCT-3' |
| mecA898-ribo | SEQ ID NO: 21 - | 5'-TGGATAGACGTCATATGA AGGTGTGCTrAC AAG/3SpC3/-3' |
| mecA990r | SEQ ID NO: 22 - | 5'-GAAAAATGATTATGGCTCAGGTACTGC -3' |
| mecA990r-bio-ribo | SEQ ID NO: 23 - | 5'-GAAAAATGATTATGGCTCAGGTACTGCrUAT CC/3SpC3/-3' |
| tuf430L | SEQ ID NO: 24 - | 5'-TGAACGTGGTCAAATCAA AGTTGGTGAA-3' |
| tuf430L-bio-ribo | SEQ ID NO: 25 - | 5'-TGAACGTGGTCAAATCAA AGTTGGTGAArAGT TG/3SpC3/-3' |
| tuf527r | SEQ ID NO: 26 - | 5' ATTTACGGAACATTTCAACACCTGTAAC-3' |
| tuf527r-bio-ribo | SEQ ID NO: 27 - | 5'-ATTTACGGAACATTTCAACACCTGTAACrAG TTG/3SpC3/-3' |

Figure 6:
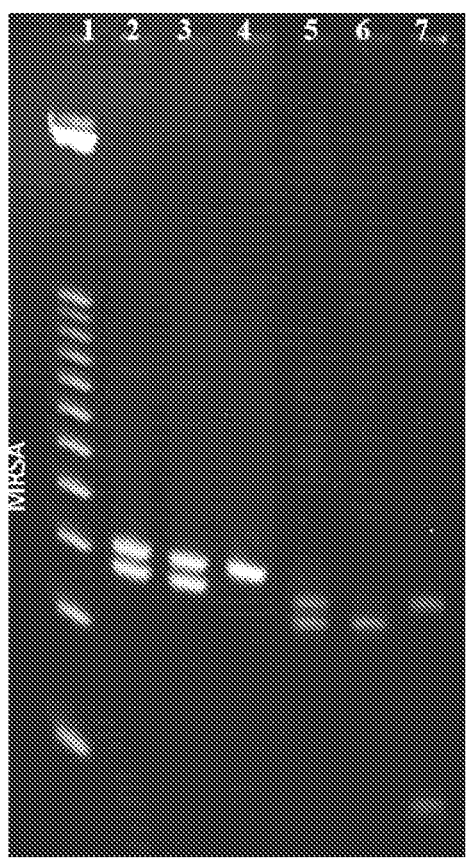
FIG. 6 shows a comparison of bpHDA and HDA for the multiplex amplification of two genes within various Staphylococcal species.

Referring to FIG. 6, a gel having 7 lanes is shown. As seen in lanes 2 and 3, bpHDA amplifies both the tuf gene and mecA gene for MRSA and MRSepi with good product balance. In the case of S. warneri (Lane 4) only the tuf gene is amplified as expected. In the case of standard HDA, MRSA is amplified with good product balance (Lane 4) but in the case of MRSepi, poor product yield is observed for the tuf gene amplification (Lane 6). For S. warneri, the tuf gene amplifies fine (Lane 7).

In one embodiment, a method of amplifying a nucleic acid sequence, includes (a) mixing a target sequence with a blocked primer, wherein the primer is modified at the 3'-end such that extension cannot take place and wherein the primer contains a single ribonucleotide; (b) contacting the mixture of target sequence and blocked primer with a thermostable RNase H2 enzyme and HDA amplification reagents; (c) heating the mixture of the product of step b, thereby deblocking the primer. In some embodiments, the HDA amplification reagents are thermostable. In some embodiments, the helicase-dependent amplification reagents extend the unblocked primer to produce a double stranded amplicon which is denatured into a single stranded nucleic acid amplicon that can hybridize to a blocked primer.

In some embodiments, the RNase H2 enzyme is present at a concentration of 1 mU/μL or greater. In some embodiments, the RNase H2 enzyme is present at a concentration of 3 mU/μL or greater.

In some embodiments, the blocked primer is represented by the general formula: 5'-dNa-Nb-dNc-X-3'; wherein a is an integer of 11 or more; b is an integer of 1; c is an integer of 1 or more; dN is a deoxyribonucleotide or nucleotide analog; N is an unmodified ribonucleotide and/or modified ribonucleotide; X is a deoxynucleotide, nucleotide, nucleotide analog, or nonnucleotide modification such that extension by DNA polymerase cannot take place; wherein the Nb-dNc-X portion constitutes a primer flap. In some embodiments, the primer flap contributes greater than 2° C. to the melting temperature of the primer. In some embodiments, the primer flap consists of at least 3 base pairs and includes at least one cytosine or guanosine base. In some embodiments, the primer flap does not have a cytosine or guanosine base and consists of at least 4 base pairs. In some embodiments, the primer flap has no cytosine or guanosine and consists of at least 2 bases selected from a modified base and minor groove binder. In some embodiments, the primer is deblocked within about 15 minutes using a cleavage assay containing 10 mU/μL of RNase H2, 200 nM target sequence and 400 nM blocked primer incubated at 70° C. In some embodiments, the amplified DNA produced by the method is detectable in less than about 60 minutes. In some embodiments, the amplified DNA produced by the method is detectable in less than about 30 minutes. In some embodiments, the HDA amplification reagents are selected from the group consisting of: buffer, DNA polymerase, helicase, optionally single stranded binding protein and deoxynucleotide triphosphates, and combinations of the same.

In another aspect, a composition is disclosed containing (a) a blocked primer having a flap comprising a single ribonucleotide at its 5' end and a blocking modification at its 3'-end such that extension by DNA polymerase cannot take place; (b) a thermostable RNase H enzyme and (c) thermostable helicase-dependent amplification reagents.

What is claimed is:

1. A system for diagnostic testing, comprising:
a blocked primer which includes a flap comprising a single ribonucleotide at its 5'end and a blocking modification at its 3' end;
thermostable RNase H enzyme; and
thermostable helicase-dependent amplification reagents, comprising: buffer, DNA polymerase, helicase, and deoxynucleotide triphosphates.

2. The system of claim 1, wherein the RNase H enzyme is RNase H1.

3. The system of claim 1, wherein the RNase H enzyme is RNase H2.

4. The system of claim 1, wherein the blocked primer is of the formula: 5'-dNa-Nb-dNc-X-3'
wherein a is an integer of 11 or more;
b is an integer of 1;
c is an integer of 1 or more;
dN is a deoxyribonucleotide or nucleotide analog;
N is an unmodified ribonucleotide or modified ribonucleotide;
X is a deoxynucleotide or nucleotide lacking a 3'-hydroxyl group nucleotide analog, or nonnucleotide modification such that extension by DNA polymerase cannot take place.

5. The system of claim 4, wherein the primer flap contributes greater than 2° C. to the melting temperature of the primer.

6. The system of claim 4, wherein the primer flap consists of at least 3 base pairs and includes at least one cytosine or guanosine base.

7. The system of claim 5, wherein the primer flap consists of at least 3 base pairs and includes at least one cytosine or guanosine base.

8. The system of claim 4, wherein the primer flap does not have a cytosine or guanosine base and consists of at least 4 base pairs.

9. The system of claim 5, wherein the primer flap does not have a cytosine or guanosine base and consists of at least 4 base pairs.

10. The system of claim 4, wherein the primer flap has no cytosine or guanosine and consists of at least 2 bases selected from a modified base and minor groove binder.

11. The system of claim 5, wherein the primer flap has no cytosine or guanosine and consists of at least 2 bases selected from a modified base and minor groove binder.

12. The system of claim 1, wherein the blocked primer when added to the thermostable helicase-dependent amplification reagents is present in a concentration greater than 50 nM.

13. The system of claim 2, wherein the blocked primer when added to the thermostable helicase-dependent amplification reagents is present in a concentration greater than 50 nM.

14. The system of claim 3, wherein the blocked primer when added to the thermostable helicase-dependent amplification reagents is present in a concentration greater than 50 nM.

15. The system of claim 4, wherein the blocked primer when added to the thermostable helicase-dependent amplification reagents is present in a concentration greater than 50 nM.

16. The system of claim 5, wherein the blocked primer when added to the thermostable helicase-dependent amplification reagents is present in a concentration greater than 50 nM.

17. The system of claim 6, wherein the blocked primer when added to the thermostable helicase-dependent amplification reagents is present in a concentration greater than 50 nM.

18. The system of claim 7, wherein the blocked primer when added to the thermostable helicase-dependent amplification reagents is present in a concentration greater than 50 nM.

19. The system of claim 8, wherein the blocked primer when added to the thermostable helicase-dependent amplification reagents is present in a concentration greater than 50 nM.

20. The system of claim 9, wherein the blocked primer when added to the thermostable helicase-dependent amplification reagents is present in a concentration greater than 50 nM.

21. The system of claim 10, wherein the blocked primer when added to the thermostable helicase-dependent amplification reagents is present in a concentration greater than 50 nM.

22. The system of claim 11, wherein the blocked primer when added to the thermostable helicase-dependent amplification reagents is present in a concentration greater than 50 nM.

\* \* \* \* \*